US009448343B2

(12) United States Patent
Kvamme et al.

(10) Patent No.: US 9,448,343 B2
(45) Date of Patent: Sep. 20, 2016

(54) SEGMENTED MIRROR APPARATUS FOR IMAGING AND METHOD OF USING THE SAME (71) Applicant: KLA-Tencor Corporation, Milpitas, CA (US)

(72) Inventors: Damon Kvamme, Los Gatos, CA (US); Frank Chilese, San Ramon, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 254 days.

(21) Appl. No.: 13/837,765

(22) Filed: Mar. 15, 2013

(65) Prior Publication Data

US 2014/0264051 A1 Sep. 18, 2014

(51) Int. Cl.
*G01N 21/88* (2006.01)
*G02B 5/08* (2006.01)
*G02B 5/09* (2006.01)
*G03F 1/84* (2012.01)
*G01N 21/956* (2006.01)

(52) U.S. Cl.
CPC .......... *G02B 5/0891* (2013.01); *G01N 21/8806* (2013.01); *G02B 5/09* (2013.01); *G03F 1/84* (2013.01); *G01N 21/956* (2013.01)

(58) Field of Classification Search
CPC .................................. G01J 1/429; G01N 21/39
See application file for complete search history.

(56) References Cited

U.S. PATENT DOCUMENTS

| 5,563,702 | A | 10/1996 | Emery et al. |
| 5,572,598 | A | 11/1996 | Wihl et al. |
| 5,691,541 | A * | 11/1997 | Ceglio et al. ............... 250/492.1 |
| 5,737,072 | A | 4/1998 | Emery et al. |
| 5,966,677 | A | 10/1999 | Fiekowsky |
| 6,052,478 | A | 4/2000 | Wihl et al. |
| 6,076,465 | A | 6/2000 | Vacca et al. |
| 6,167,355 | A | 12/2000 | Fiekowsky |
| 6,248,988 | B1 | 6/2001 | Krantz |
| 6,263,292 | B1 | 7/2001 | Fiekowsky |
| 6,282,309 | B1 | 8/2001 | Emery |
| 6,353,470 | B1 * | 3/2002 | Dinger ............................ 355/71 |
| 6,363,166 | B1 | 3/2002 | Wihl et al. |
| 6,381,358 | B1 | 4/2002 | Vacca et al. |
| 6,397,165 | B1 | 5/2002 | Fiekowsky |
| 6,405,153 | B1 | 6/2002 | Fiekowsky |
| 6,435,642 | B1 * | 8/2002 | Jackson ............... B41J 2/04508 347/19 |
| 6,516,085 | B1 | 2/2003 | Wiley et al. |

(Continued)

FOREIGN PATENT DOCUMENTS

WO 2012059537 5/2012

*Primary Examiner* — David Porta
*Assistant Examiner* — Djura Malevic
(74) *Attorney, Agent, or Firm* — Simpson & Simpson, PLLC (57) ABSTRACT An apparatus for inspecting a photomask, comprising an illumination source for generating a light which illuminates a target substrate, objective optics for receiving and projecting the light which is reflected from the target substrate, the objective optics includes a first mirror arranged to receive and reflect the light which is reflected from the target substrate, a second mirror which is arranged to receive and reflect the light which is reflected by the first mirror, a third mirror which is arranged to receive and reflect the light which is reflected by the second mirror, and a segmented mirror which is arranged to receive and reflect the light which is reflected by the third mirror. The segmented mirror includes at least two mirror segments. The apparatus further includes at least one sensor for detecting the light which is projected by the objective optics.

23 Claims, 3 Drawing Sheets

(56) References Cited

U.S. PATENT DOCUMENTS

| | | |
|---|---|---|
| 6,529,621 B1 | 3/2003 | Glasser et al. |
| 6,539,331 B1 | 3/2003 | Fiekowsky |
| 6,577,389 B2 | 6/2003 | Biellak et al. |
| 6,584,218 B2 | 6/2003 | Wihl et al. |
| 6,614,520 B1 | 9/2003 | Bareket et al. |
| 6,636,301 B1 | 10/2003 | Kvamme et al. |
| 6,646,281 B1 | 11/2003 | Krantz et al. |
| 6,654,489 B2 | 11/2003 | Wiley et al. |
| 6,673,638 B1 | 1/2004 | Bendik et al. |
| 6,674,522 B2 | 1/2004 | Krantz et al. |
| 6,691,052 B1 | 2/2004 | Maurer |
| 6,727,512 B2 | 4/2004 | Stokowski et al. |
| 6,731,787 B1 | 5/2004 | Vacca et al. |
| 6,748,103 B2 | 6/2004 | Glasser et al. |
| 6,760,473 B1 | 7/2004 | Fiekowsky |
| 6,836,560 B2 | 12/2004 | Emery |
| 6,844,927 B2 | 1/2005 | Stokowski et al. |
| 6,850,321 B1 | 2/2005 | Yu |
| 6,879,390 B1 | 4/2005 | Kvamme et al. |
| 6,946,670 B1 | 9/2005 | Zurbrick |
| 6,952,256 B2 | 10/2005 | Roncome et al. |
| 6,966,047 B1 | 11/2005 | Glasser |
| 6,999,611 B1 | 2/2006 | Lopez et al. |
| 7,027,143 B1 | 4/2006 | Stokowski et al. |
| 7,027,635 B1 | 4/2006 | Wihl et al. |
| 7,046,352 B1 | 5/2006 | Dayal et al. |
| 7,046,355 B2 | 5/2006 | Yu |
| 7,075,638 B2 | 7/2006 | Kvamme et al. |
| 7,106,895 B1 | 9/2006 | Goldberg et al. |
| 7,123,356 B1 | 10/2006 | Stokowski et al. |
| 7,126,681 B1 | 10/2006 | Chen et al. |
| 7,133,119 B1 | 11/2006 | Pettibone et al. |
| 7,138,640 B1 | 11/2006 | Delgado et al. |
| 7,167,185 B1 | 1/2007 | Yiin et al. |
| 7,215,409 B2 * | 5/2007 | Sandstrom ...................... 355/53 |
| 7,271,891 B1 | 9/2007 | Xiong et al. |
| 7,292,393 B2 | 11/2007 | Kvamme |
| 7,295,301 B2 | 11/2007 | Yu |
| 7,295,695 B1 | 11/2007 | Dayal |
| 7,297,453 B2 | 11/2007 | Watson et al. |
| 7,300,725 B2 | 11/2007 | Watson et al. |
| 7,300,729 B2 | 11/2007 | Watson et al. |
| 7,303,842 B2 | 12/2007 | Watson et al. |
| 7,352,457 B2 | 4/2008 | Kvamme et al. |
| 7,379,175 B1 | 5/2008 | Stokowski et al. |
| 7,379,847 B1 | 5/2008 | Blecher et al. |
| 7,440,093 B1 | 10/2008 | Xiong et al. |
| 7,453,561 B2 * | 11/2008 | Uto ....................... G01N 21/47 356/237.2 |
| 7,483,146 B1 | 1/2009 | Zorabedian |
| 7,486,393 B2 | 2/2009 | Kvamme et al. |
| 7,493,590 B1 | 2/2009 | Hess et al. |
| 7,499,156 B2 | 3/2009 | Chen et al. |
| 7,538,856 B2 * | 5/2009 | Kajiyama et al. .............. 355/67 |
| 7,541,115 B2 | 6/2009 | Volk et al. |
| 7,546,573 B1 | 6/2009 | Verma et al. |
| 7,564,545 B2 | 7/2009 | Stokowski |
| 7,580,124 B2 | 8/2009 | Yu |
| 7,583,433 B2 * | 9/2009 | Antoni et al. ................. 359/351 |
| 7,599,051 B1 | 10/2009 | Labovitz et al. |
| 7,604,906 B1 | 10/2009 | Volk et al. |
| 7,646,906 B2 | 1/2010 | Saidin et al. |
| 7,664,310 B2 | 2/2010 | Emery |
| 7,689,966 B2 | 3/2010 | Verma et al. |
| 7,724,360 B2 * | 5/2010 | Uto ....................... G01N 21/47 356/237.1 |
| 7,724,939 B2 | 5/2010 | Goldberg et al. |
| 7,734,711 B1 | 6/2010 | Blecher et al. |
| 7,738,092 B1 | 6/2010 | Stokowski |
| 7,738,093 B2 | 6/2010 | Alles et al. |
| 7,746,459 B2 * | 6/2010 | Kadkly .............. G01N 21/9501 356/237.2 |
| 7,764,385 B1 * | 7/2010 | Dey ............................... 356/518 |
| 7,769,225 B2 | 8/2010 | Kekare et al. |
| 7,788,629 B2 | 8/2010 | Zurbrick et al. |
| 7,835,015 B1 | 11/2010 | Wright et al. |
| 7,873,204 B2 | 1/2011 | Wihl et al. |
| 7,926,959 B1 | 4/2011 | Kvamme et al. |
| 7,932,004 B1 | 4/2011 | Xiong et al. |
| 7,962,863 B2 | 6/2011 | Su et al. |
| 7,995,199 B2 | 8/2011 | Hess et al. |
| 7,995,832 B2 | 8/2011 | Xiong et al. |
| 8,089,038 B1 | 1/2012 | Latypov |
| 8,090,189 B1 | 1/2012 | Phalke et al. |
| 8,102,408 B2 | 1/2012 | Verma et al. |
| 8,103,086 B2 | 1/2012 | Shi et al. |
| 8,151,220 B2 | 4/2012 | Hess et al. |
| 8,165,384 B1 | 4/2012 | Ma et al. |
| 8,204,297 B1 | 6/2012 | Xiong et al. |
| 8,498,468 B1 | 7/2013 | Volk |
| 8,624,971 B2 * | 1/2014 | Brown ............... G01N 21/9501 348/126 |
| 8,629,972 B2 * | 1/2014 | Zellner et al. ................... 355/67 |
| 8,711,346 B2 * | 4/2014 | Stokowski ............ B82Y 10/00 356/237.2 |
| 2002/0093636 A1 * | 7/2002 | Komatsuda ...................... 355/67 |
| 2002/0126888 A1 | 9/2002 | Vacca et al. |
| 2002/0145718 A1 * | 10/2002 | Dinger ............................ 355/67 |
| 2003/0071204 A1 * | 4/2003 | Sandstrom et al. ...... 250/237 G |
| 2003/0138138 A1 | 7/2003 | Vacca et al. |
| 2004/0012866 A1 * | 1/2004 | Mann et al. ................... 359/857 |
| 2004/0051857 A1 * | 3/2004 | Hudyma et al. ................ 355/67 |
| 2004/0095573 A1 * | 5/2004 | Tsai .................. G01N 21/8806 356/237.5 |
| 2004/0096094 A1 | 5/2004 | Vacca et al. |
| 2005/0140957 A1 * | 6/2005 | Luijkx et al. .................... 355/71 |
| 2005/0140970 A1 | 6/2005 | Vacca et al. |
| 2005/0174650 A1 | 8/2005 | Melzer et al. |
| 2006/0232867 A1 * | 10/2006 | Mann et al. ................... 359/858 |
| 2007/0140548 A1 | 6/2007 | Vacca et al. |
| 2008/0133160 A1 | 6/2008 | Vacca et al. |
| 2008/0316451 A1 * | 12/2008 | Mann .................. G02B 13/143 355/53 |
| 2009/0011345 A1 | 1/2009 | Tinnemans et al. |
| 2009/0027641 A1 * | 1/2009 | Kajiyama et al. .............. 355/53 |
| 2009/0040525 A1 * | 2/2009 | Kadkly .............. G01N 21/9501 356/446 |
| 2009/0079973 A1 * | 3/2009 | Uto ....................... G01N 21/47 356/237.2 |
| 2009/0324054 A1 | 12/2009 | Vacca et al. |
| 2010/0080647 A1 * | 4/2010 | Terasawa et al. .................. 403/5 |
| 2010/0231882 A1 * | 9/2010 | Dinger et al. ................... 355/67 |
| 2010/0231884 A1 * | 9/2010 | Mann ............................... 355/67 |
| 2010/0231885 A1 * | 9/2010 | Mann ............................... 355/67 |
| 2010/0259742 A1 * | 10/2010 | Singer ............................. 355/67 |
| 2011/0019206 A1 | 1/2011 | Wright et al. |
| 2011/0026003 A1 * | 2/2011 | Zellner et al. ................... 355/71 |
| 2011/0090559 A1 * | 4/2011 | Rennon et al. ............... 359/351 |
| 2011/0116077 A1 | 5/2011 | Chuang et al. |
| 2011/0242544 A1 * | 10/2011 | Stroessner et al. ........... 356/496 |
| 2011/0299758 A1 | 12/2011 | Shi et al. |
| 2012/0032065 A1 | 2/2012 | Armstrong |
| 2012/0086799 A1 | 4/2012 | Hess |
| 2012/0182533 A1 * | 7/2012 | Schoeppach et al. .......... 355/66 |
| 2012/0235049 A1 | 9/2012 | Wang |
| 2012/0236281 A1 | 9/2012 | Wang et al. |
| 2012/0238096 A1 | 9/2012 | Xiong et al. |
| 2012/0274924 A1 | 11/2012 | Delgado |
| 2013/0038850 A1 * | 2/2013 | Feldmann et al. .............. 355/67 |
| 2013/0063803 A1 | 3/2013 | Delgado et al. |
| 2013/0083321 A1 * | 4/2013 | Wack et al. ................. 356/239.3 |
| 2013/0088245 A1 | 4/2013 | Sezginer |
| 2013/0111417 A1 | 5/2013 | Hess et al. |
| 2013/0176552 A1 | 7/2013 | Brown et al. |
| 2013/0242278 A1 * | 9/2013 | Enkisch et al. ................. 355/71 |

* cited by examiner

SEGMENTED MIRROR APPARATUS FOR IMAGING AND METHOD OF USING THE SAME

FIELD OF THE INVENTION

The present invention broadly relates to optical apparatus and methods of using the same, and, more particularly, to an optical apparatus having a segmented mirror for imaging and, even more particularly, to an optical apparatus and method for inspecting a photomask using light imaging.

BACKGROUND OF THE INVENTION

The conventional apparatus in the market for photomask inspection generally employ ultra-violet (UV) light with wavelengths at or above 193 nanometers (nm). This is suitable for masks designed for use in lithography based on 193 nm light. To further improve the printing of minimum feature sizes, next generation lithographic equipment is now designed for operation in the neighborhood of 13.5 nm. Accordingly, patterned masks designed for operation near 13 nm must be inspected. Such masks are reflective, having a patterned absorber layer over a resonantly-reflecting substrate (EUV multilayer), typically 40 pairs of molybdenum silicide (MoSi) with a 7 nm period. The conventional inspection apparatus uses optics with a combination of wavelength and numerical apertures (NA) that are not sufficient (i.e., too small) to resolve pattern features and pattern defects of interest (printable) in EUV mask patterns characterized by a half-pitch below 22 nm.

As part of the optics in the conventional inspection apparatus, mirrors of varying sizes and shapes are used to receive and reflect EUV light reflected from the substrate. To keep the telecentric condition at the image plane, some mirrors are notably large in size (e.g., 280 mm by 200 mm). The sheer size of the mirror significantly increases the cost of production. Moreover, large mirrors require an increased thickness to reduce self-weight distortion, which adds to the overall cost of production.

Mounting a large mirror in an inspection device requires a robust mounting structure to reduce self-weight distortion and to reduce the static movement of the mirror in rigid body motion due to the large mirror weight deflecting the main structure. The configuration of the mounting structure should protect against distortion or unacceptable motion of a large mirror. In addition, a large mirror may require a graduated or indexed coating to meet distortion needs. Adding a graduated or indexed coating to a large mirror adds complexity to the manufacturing process.

During the mirror manufacturing and inspection process, mirrors are tested to ensure they receive and reflect light as intended. Large mirrors are more expensive and difficult to test. When a large mirror is removed from the mounting structure, technicians must protect the mirror from distorting under its own weight. Moreover, numerous test points are required for large mirrors due to the number of small sub-apertures. This additional testing requires more labor and time to validate the mirror. If the testing uncovers variations or defects in the mirror surface, the mirror must be reworked to fix the variation or defect. Rework can be a continual process, which impacts yield and cost.

Thus, there is a long-felt need for an invention to improve upon the shortcomings of large mirrors that would reduce mirror distortion and improve testing efficiency. More specifically, there is a long-felt need for a segmented mirror apparatus for light imaging and a method of using the same.

SUMMARY OF THE INVENTION

The present invention broadly comprises an apparatus for inspecting a photomask using a light, including an illumination source for generating light which illuminates a target substrate, objective optics for receiving and projecting the light which is reflected from the target substrate, the objective optics including, a first mirror arranged to receive and reflect the light which is reflected from the target substrate, a second mirror which is arranged to receive and reflect the light which is reflected by the first mirror, a third mirror which is arranged to receive and reflect the light which is reflected by the second mirror, and, a segmented mirror which is arranged to receive and reflect the light which is reflected by the third mirror, wherein the segmented mirror includes at least two mirror segments. The apparatus further includes at least one sensor for detecting the light which is projected by the objective optics.

A general object of the invention is to replace one large parent mirror with a plurality of smaller mirror segments. These mirrors are lighter and easier to mount. In addition, small mirrors have less surface distortion due to mounting and self-weight. Smaller mirror segments are easier to handle during testing and require fewer test points.

Another object of the invention is to use identical mirror segments when the parent mirror is spherical. Using identical mirror segments to form a spherical shape reduces manufacturing complexity. If the parent mirror is ashperical, each mirror segment could be a best fit sphere close enough to the parent asphere that the combination of the spheres will not degrade the image quality unacceptably.

Yet another object of the invention is to provide uniform mirror coatings. Instead of having a single large mirror with a graduated coating, each mirror segment may use a different coating to mimic the effect of a graduated coating. Each smaller mirror segment would have a continuous, non-graduated coating. One mirror segment coating would, in isolation, be continuous, but when viewed as a grouping of mirror segments, would mimic the graduated profile of a large mirror.

These and other objects and advantages of the present invention will be readily appreciable from the following description of preferred embodiments of the invention and from the accompanying drawings and claims.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

At the outset, it should be appreciated that like drawing numbers on different drawing views identify identical, or functionally similar, structural elements of the invention. It also should be appreciated that figure proportions and angles are not always to scale in order to clearly portray the attributes of the present invention.

While the present invention is described with respect to what is presently considered to be the preferred aspects, it is to be understood that the invention as claimed is not limited to the disclosed aspects. The present invention is intended to cover various modifications and equivalent arrangements included within the spirit and scope of the appended claims.

Furthermore, it is understood that this invention is not limited to the particular methodology, materials and modifications described and, as such, may, of course, vary. It is also understood that the terminology used herein is for the purpose of describing particular aspects only, and is not intended to limit the scope of the present invention, which is limited only by the appended claims.

Although any methods, devices or materials similar or equivalent to those described herein can be used in the practice or testing of the invention, the preferred methods, devices, and materials are now described.

Extreme ultra-violet (EUV) microscope objectives (having 2 to 4 multilayer-coated mirrors) have been disclosed previously, are designed for defect or pattern review applications, with operation in the neighborhood of 13.5±0.5 nm wavelength of light, have a NA in the range 0.05-0.12, and an object field extent just adequate to the review (microscopy) task, i.e., in the range of 5-20 microns at the mask. According to rigorous analyses of the defect detection capability as a function of NA and defect size, the resolving power and defect detection sensitivity of EUV objectives with NA in this range are inadequate for production-worthy EUV inspection of masks with feature half-pitch (HP) below 18 nm or so, due to shortcomings in both NA and high-quality object field size.

Current mask inspection systems are based on UV and deep ultra-violet (DUV) laser sources of light, which are high brightness and relatively high power. Light sources with significant spectral brightness in the neighborhood of 13.5 nm are based on pulsed plasmas. Due to poor conversion efficiency (conversion from input energy to in-band radiation), such plasma sources show limited brightness at 13-14 nm, and raising the brightness significantly can drive source cost (and thus inspection costs imposed on the mask during fabrication) to levels which impair the economic attractiveness of EUV Lithography (EUVL).

High-throughput operation of mask inspection systems with low brightness plasma sources (discharge or laser produced) drives the need for large object fields and detector arrays, to increase the rate of instantaneous image signal integration and conversion to digital representation.

Simultaneously, to discriminate defect signals from background image noise, the imaging optics must maximize the collection of light diffracted or scattered by patterning or multilayer defects residing on the EUV mask of interest. For most defects of interest, which diffract and scatter the incident light over a wide range of angles, increasing the NA of the objective will provide an increase in defect signals.

Multilayer-mirror based imaging systems have poor transmission of light, due to the limited reflectivity of multilayers at the design wavelengths near 13-14 nm. A single MoSi multilayer mirror shows peak spectral reflectivity near 13.5 nm in the range of 60-70%. After multiple reflections from near-normal incidence mirrors in typical illumination and imaging optics in an EUV system, system transmission can fall below 1%. It should be appreciated that decreased system transmission can also occur due to the cumulative effect of several factors, e.g., mirror reflections (normal and grazing), gas transmission and debris migration.

To perform the inspection task adequately, the light reaching the image plane and converted to digital signals by the detector array, from each resolved region of the mask, must reach a certain number of primary (13.5 nm) quanta, and so a certain minimum signal-to-noise ratio, which in well-designed systems is a strong function of the number of primary quanta (photons absorbed in the detector material, typically silicon). To compensate for losses in the optical system while keeping the light incident on the detector constant, the source brightness must be increased, which is difficult to develop and expensive to produce using currently known source technologies.

Alternatively, the range of angles emitted by the source which are transferred to the mask by the illumination optics can be increased, since the amount of light will increase with this angular range, at least within a range of angles supported by the source brightness. In other words, the illumination pupil size can be increased until a physical constraint intervenes. Rigorous studies of defect signal to noise ratio (SNR) in inspection optic designs have indicated that for EUV masks, such largely incoherent imaging often provides higher SNR than lower sigma, more coherent operation of the design and system, when used with plasma sources of limited brightness.

The use of beam splitters in reflective imaging systems used in conjunction with reflective objects (such as EUV mask inspection using EUV light) can simplify optical design and layout, by allowing interpenetration or overlap of illumination and imaging pupils in angle space. Current EUV beam splitter technologies have low reflection and transmission coefficients (25-35%). Inspection systems with beam splitters must increase source brightness greatly to compensate for the loss of light reaching the detector. Inspection optics without a beam splitter element is thus strongly preferred.

Light at wavelengths within the spectral bandpass of the resonantly-reflecting multilayer incident on such a uniform (unpatterned) mirror is reflected at 60-70% only if the angle of incidence resides within the angular bandpass as well. Bandpass refers to a type of filter or filtering process. Periodic MoSi multilayers have an angular bandpass of 20-25 degrees at 13.5 nm. Light incident outside of the angular bandpass is reflected by the multilayer at very low levels, and thus is largely absorbed, or wasted.

Rigorous studies of light propagation and diffraction by patterns on EUV masks indicate that this trend holds for light incident on patterned masks, as well. Furthermore, the angular distribution of light diffracted and scattered by defects present on or in the EUV patterned mask is also modulated by the angular bandpass of the multilayer. The angular distribution of light scattered by a defect depends as well on the defect geometry, and the geometry of the local pattern, and can be significantly skewed to one side of the imaging pupil or another. To collect adequate light from all defect types and for arbitrary pattern geometries, the size of the imaging pupil should be maximized. Consequently, design of inspection optics without a beam splitter and which operate largely within the finite angular bandwidth of the mask, and which utilize plasma sources of limited brightness, must contend with competing angular claims of the illumination and imaging pupils, each of which seek to maximize the size of their angular extent.

EUVL at 11 HP may use aperiodic multilayers in the EUV mask design, which provide increased angular bandwidth, and enable EUVL imaging at higher NAs than possible with a conventional periodic multilayer design. This improves, but does not fully mitigate the issue of finite angular bandpass.

Although increasing the number of mirrors in an imaging design can provide design capability which enables simultaneous high NA and wide object field; this can lead to a prohibitive decrease in light reaching the detector. Thus, there is significant value in discovering designs which provide adequate inspection performance at minimum mirror count, which do not use a beam splitter, and which balance the competing needs of illuminating and imaging pupil sizes and locations, and thereby enable the production use of low brightness plasma-based EUV sources.

Furthermore, it is of strong economic interest to discover optical designs which provide adequate defect inspection performance for at least two technology nodes, for example 16 HP and 11 HP. As the critical defect size which limits chip yield shrinks with technology node, the NA of the inspection system should be increased to compensate for the reduction in scattered light.

In summary, conventional apparatus that utilize UV light are clearly limited when applied to inspect extreme ultraviolet photomasks ("EUV masks"). The conventional apparatus are typically "non-actinic" in that they result in an image of the mask that does not represent what will be realized using EUV light during lithography. Rather, the resultant image of the mask lacks both resolution and contrast, such that the image is not very useful for pattern inspection and defect detection.

More recently, photomask inspectors that use EUV light for imaging ("EUV inspectors") are being developed. However, the current EUV inspectors also have limitations and drawbacks. First, the field sizes of the images are very small. This limitation results in a low throughput when the apparatus is used to inspect entire EUV masks for defects. Second, numerical apertures of the optics are low. This limitation results in a relatively lower resolution. Such lower resolution limits the practical use of the images for pattern inspection and defect detection.

The present patent application discloses a reflective, segmented imaging apparatus that overcomes the above-discussed problems with photomask inspectors.

During inspection of patterned masks, acquisition and subsequent signal processing of the signal corresponding to a localized defective pattern can be accomplished by comparing or differencing the digital images from a test region of a pattern and a reference region, whether acquired or synthesized from prior information. The differencing operation removes the pattern, leaving the defect as a perturbation of a quasi-uniform background signal.

Imaging pupils are often circularly symmetric, leading to symmetric point spread functions (psf) at the image plane. While such symmetry is often required in lithography, mask inspection via difference imaging does not require symmetric psf, and consequently the imaging pupil can afford to be asymmetric. In particular, obscuration of a portion of the imaging pupil can be tolerated, if defect signal collection is not compromised significantly.

Additionally, the shape of the parent pupil need not be circular. For instance, square or rectangular shapes for the parent are possible, and even advantageous when considering the incremental gain of scattered defect light or signal through addition of pupil region.

Expressed as a fraction of pupil area, obscuration fractions less than 5 or 10% are preferred. Obscuration in 4-mirror designs is often created through the blocking or shadowing of light reflected or scattered from the mask by the second mirror, or M2. Minimizing the size of both reflecting surface and peripheral support of M2 will minimize obscuration.

The design of structural support for M2 must provide for sufficient rigidity that environmental disturbances or vibrations do not drive or lead to dynamic perturbations of the M2 position and thus to degradation of image quality through blurring.

Since mirrors for EUV light must be coated with multilayers to reach adequate reflectivity, the range of incidence angles on any of the highly curved elements must be considered, and restricted within the limits of multilayer deposition process technology. When estimating the defect SNR of a particular objective and system design, the apodization or modulation of transmission of each light ray by local reflectivity variations at the point of reflection on each mirror induced by the multilayer deposition process must be considered.

In particular, the design process must balance obscuration, structural response and curvature factors in the geometry of the second mirror or M2, in order to secure the minimum viable defect SNR which enables fast and economic mask inspection.

The choice of chief ray in design of the objective for mask inspection must balance several competing factors. The chief ray is defined by the centroid of the angular distribution of light rays transmitted by the objective to the image plane, with due consideration of the pupil apodization caused by mirror coatings. Although conventional designs for reflective imaging without a beam splitter place the plane dividing the illumination and collection light bundles on the optical axis and coincident with the object surface normal, inspection-oriented optics do not demand or strongly prefer this choice. Thus, allowing placement of the lower marginal ray of the imaging pupil below the surface normal is found to be advantageous for defect signal collection.

Correspondingly, in the process of increasing defect SNR, as the NA is increased from low levels, in higher performance designs the imaging chief ray (relative to the surface normal) is below the numerical value of the NA. Inspection-optimized EUV objective designs bias the imaging chief rays toward the surface normal to maximize overlap of imaging pupil with multi-layer modulated angular distribution of light scattered by pattern defects, while providing sufficient angular range (still largely restricted to the multilayer angular bandpass) to the illumination pupil to secure adequate photon flux from the limited brightness plasma EUV sources.

Within the optics configuration, the fourth mirror, or M4, in a preferred embodiment, comprises a group of mirror segments instead of a single large mirror. A single mirror segment is smaller than the parent mirror and grouped with at least one other mirror segment. Placing the mirror segments in specific configurations will create the desired shape of the parent mirror, such as spherical, aspherical, or planar. However, the grouping of mirror segments need not match the exact shape of the single parent mirror. The mirror segments are configured to optimally receive and reflect light from the third mirror, M3, to a sensor.

Since M4 is functionally near a field plane, the positional accuracy is not as severe when compared to other systems utilizing segmented mirrors, such as astronomical telescopes. In an example embodiment, each individual mirror segment supports the imaging of a sub-field that is the size of one time delay integration (TDI) sensor, as part of the sensor array.

Using multiple mirror segments allows for lighter and easier mounting compared to a single large mirror. Mirrors are removed from the imaging apparatus during testing. Removing smaller mirror segments is less demanding for technicians. As the mirror gets larger, there is a greater likelihood of distortion. Smaller mirror segments will exhibit lower surface distortion from mounting and from the mirror's own weight.

In an example embodiment where M4 is spherical in shape, the mirror segments are identical and can be manufactured in large batches. The spherical nature of the mirror permits the use of identical mirror segments to form substantially the same spherical shape as a single large mirror. For an aspherical M4 shape, another embodiment, the mirror segments are distinct and configured into a best fit asphere close enough to the original asphere that it would not appreciably degrade image quality. However, the configuration of mirror segments does not have to mimic the shape of the parent mirror.

For a single large mirror, a graduated or indexed coating is typically applied to meet distortion needs. By using a configuration of mirror segments for M4, the variations in coating may be achieved by varying the coating on each mirror segments. Instead of a graduated or indexed coating on one large mirror, the coating on each mirror segment will be designed to meet the optical needs of M4. Each mirror segment will have a uniform coating with a distinct coating period. This will significantly reduce manufacturing costs.

Using a mounting structure, each mirror segment is fixed relative to the other mirror segments. The mirror segments do not have to be directly connected to each other. Their positioning is dependent upon the desired optics configuration. Individually, the mirror segments are aligned relative to the mounting structure during assembly or setup. Configuration may be performed by a technician or through a computer-controlled mounting system.

Figure 1:
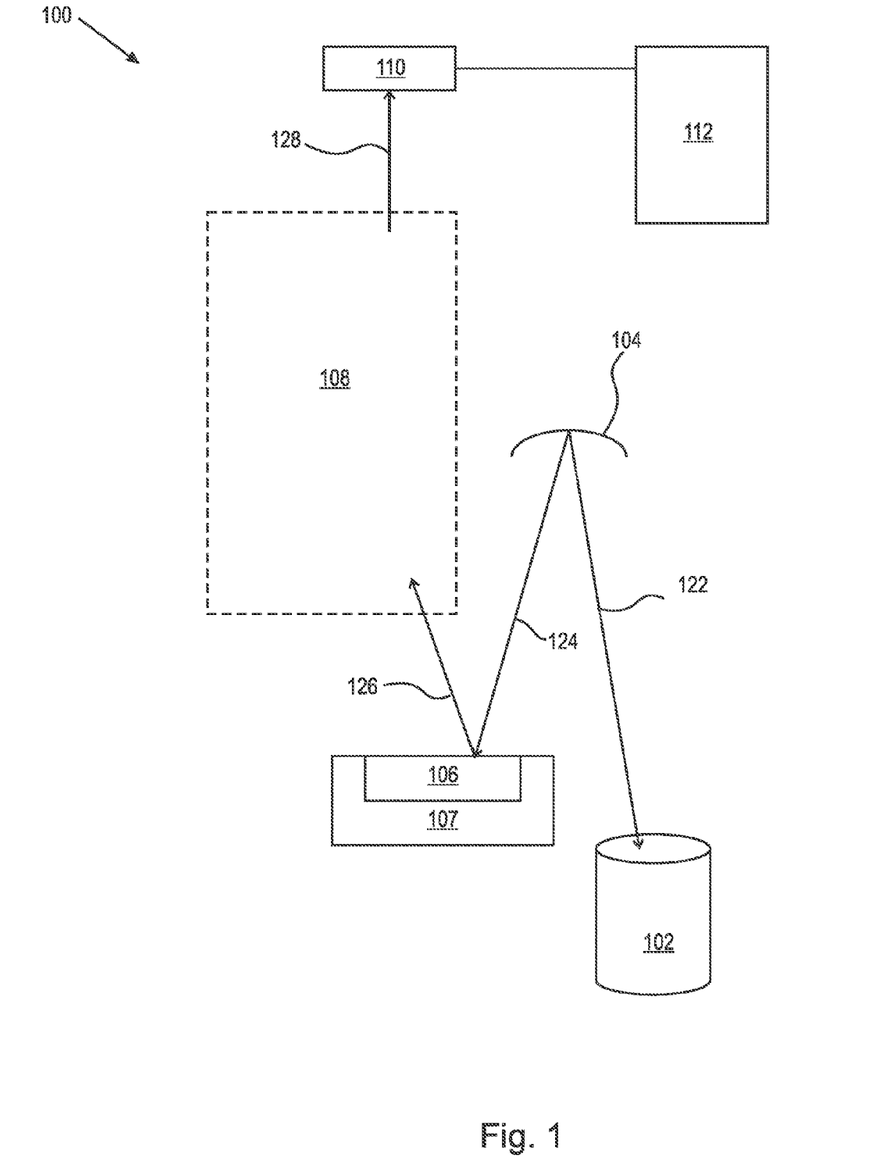
FIG. 1 is a schematic diagram of a reflective imaging apparatus in accordance with an embodiment of the invention.

Adverting now to the drawings, FIG. 1 is a schematic diagram of a reflective imaging apparatus in accordance with an embodiment of the invention. Apparatus 100 includes EUV illumination source 102, illumination mirror 104, target substrate 106, substrate holder 107, objective optics 108, sensor (detector) 110, and data processing system 112.

EUV illumination source 102 may comprise, for example, a laser-induced plasma source which outputs EUV light beam 122. In one embodiment, the EUV light is at a wavelength of 13.5±0.5 nm. Illumination mirror 104 reflects the EUV light such that beam 124 illuminates target substrate 106. In one embodiment of the invention, target substrate 106 is an EUV mask being inspected. Target substrate 106 may be scanned under beam 124 by controllably translating substrate holder 107 so that the field of view of the imaging apparatus covers regions on the substrate to be inspected.

Patterned light 126 is reflected from target substrate 106 to reflective objective optics 108. A preferred embodiment of objective optics 108 is described in detail below in relation to FIG. 2.

Objective optics 108 outputs projection 128 of the patterned light onto sensor 110. In one embodiment, sensor 110 may be a time-delay integration detector array so that the data may be detected while the target substrate is being scanned (translated) under beam 124.

Data processing system 112 may include electronic circuitry, one or more microprocessors, data storage, memory and input and output devices. Data processing system 112 may be configured to receive and process data from sensor 110. In accordance with one embodiment, data processing system 112 may process and analyze the detected data for pattern inspection and defect detection.

Figure 2:
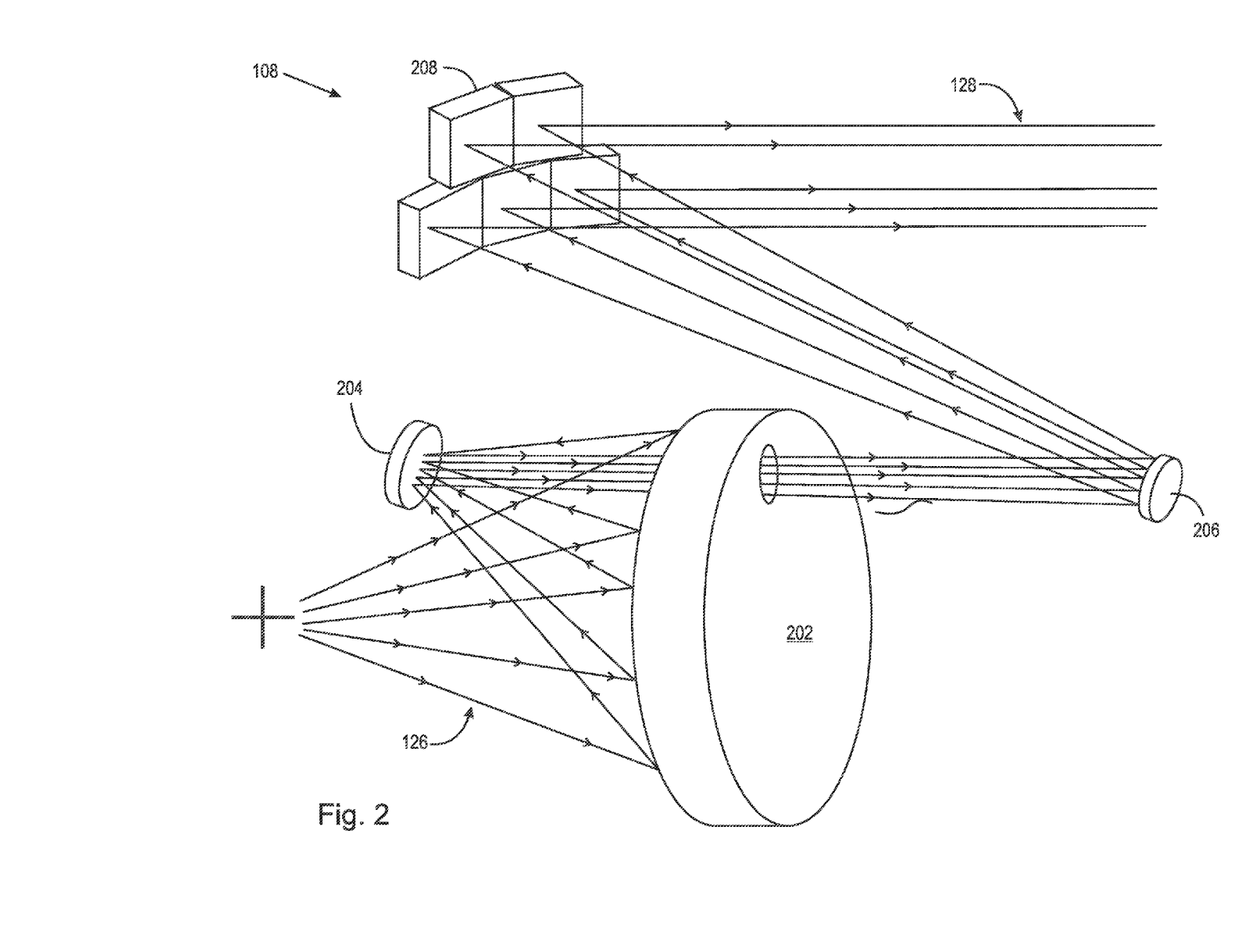
FIG. 2 is an optical ray diagram of a mirror distribution for reflective objective optics in accordance with an embodiment of the invention; and, FIG. 3 is an isolated view of a segmented fourth mirror in accordance with an embodiment of the invention.

FIG. 2 is an optical ray diagram of a mirror distribution for the objective optics 108 in accordance with one embodiment of the invention. An optical prescription for objective optics 108 in FIG. 2 is provided below in Appendix A.

In this embodiment, there are three non-segmented mirrors 202, 204, and 206 and one segmented mirror 208 arranged as shown in FIG. 2. The mirrors are arranged such that patterned light 126 reflects from the first non-segmented, second non-segmented, third non-segmented, and the segmented mirrors 202, 204, 206, and 208, respectively, in that order. In this arrangement, first non-segmented mirror 202 is concave, second non-segmented mirror 204 is convex, third non-segmented mirror 206 is concave, and segmented mirror 208 is concave. Hence, the mirrors are, in order: concave; convex; concave; and concave.

In this embodiment, second non-segmented mirror 204 partially obscures first non-segmented mirror 202 from patterned light 126. In other words, part of the area of first non-segmented mirror 202 is blocked by second non-segmented mirror 204 from receiving light 126 reflected from target substrate 106. Furthermore, an opening in first non-segmented mirror 202 is used to let the light reflected by second non-segmented mirror 204 pass through to reach third non-segmented mirror 206. It has been found that, despite first non-segmented mirror 202 being partially obscured and needing a pass-through hole, a high numerical aperture is nevertheless achieved with this embodiment.

Figure 3:
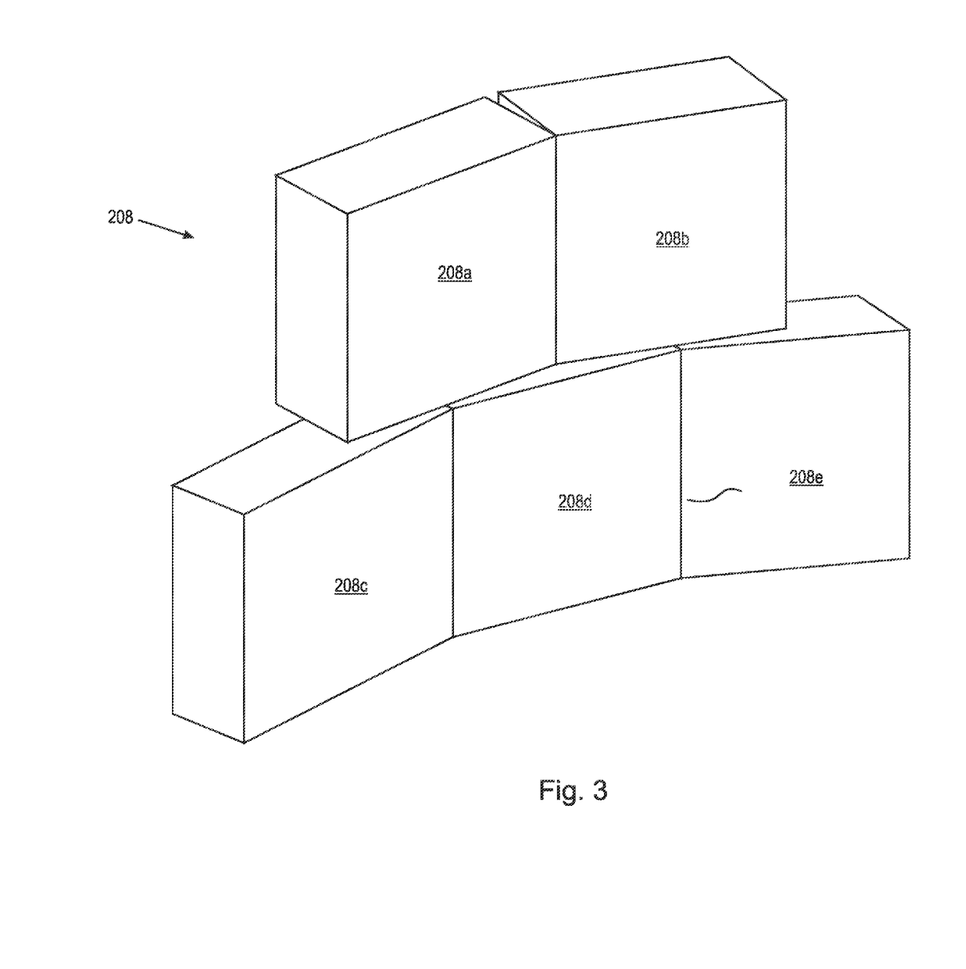

FIG. 3 is an isolated view of an embodiment of the mirror segments of the fourth mirror. Segmented mirror 208 is a grouping of mirror segments 208a, 208b, 208c, 208d and 208e that receives the light from third non-segmented mirror 206 and subsequently reflects the light to sensor 110. In this embodiment, there are five mirror segments, but it should be appreciated that there can be any number of mirror segments. In an embodiment, the grouping of mirror segments forms a spherical shape wherein each segment is identical. In an alternate embodiment, the segmented mirror comprises unique mirror segments that collectively form an aspherical shape.

In accordance with a preferred embodiment, the numerical aperture for the objective optics is at least 0.2, and the field of view is at least 5,000 square microns in area. For the embodiment of objective optics 108, described above, the numerical aperture has been determined to be 0.2 at the object plane, and the size of the field of view has been determined to be 300 microns by 400 microns (120,000 square microns in area). The field of view is offset 273 microns from the optical axis. Advantageously, both the numerical aperture and field of view are relatively large in this embodiment.

The working distance is the distance between target substrate 106 and the nearest optical element (in this case, the second mirror 204). A working distance of at least 100 millimeters (mm) is desirable to provide sufficient space for illumination of the target substrate 106. In this embodiment, the working distance is 174 mm.

The magnification represents how much larger an object at the mask plane will appear at the sensor plane. Based on the characteristics of the spherical embodiment, described above, the magnification is 711.1×.

Although the use of EUV light is discussed to describe a preferred embodiment of the present invention, light at other wavelength ranges can also be used as an illumination source. For example, the present invention can be configured to use ultra-violet light, visible light, as well as light at other wavelengths as the illumination source. The photomask or other object, surface, pattern, etc. being imaged will dictate the required wavelength used in the inspection tool.

objective optics to the at least one sensor, wherein a respective mirror segment in the segmented mirror supports the imaging of a sub-field equal to a size of a single time delay integration sensor.

APPENDIX A

Optical Prescription for Objective Optics depicted in FIG. 2.

| ELT NO. | SUR NO. | SURFACE RADIUS X | Y | DESCRIPTION SHAPE | THICKNESS OR SEPARATION | APERTURE DESCRIPTION DIMENSION X | Y | SHAPE | MATERIAL |
|---|---|---|---|---|---|---|---|---|---|
| OBJECT | | INF | | FLT | 0.0000 | 0.945 | | CIR | |
| | 1 | DECENTER(1) RETURN(1) | | | 292.6339 337.3662 | 119.467 | | CIR | (STOP) |
| 1 | 2 | −508.391 | | A-1 | −455.0115 | 440.955 | | CIR | REFL |
| 2 | 3 | 56.050 | | A-2 | 925.0114 | 30.080 | | CIR | REFL |
| 3 | 4 | 48.906 | | A-3 | −600.0001 | 21.163 | | CIR | REFL |
| 4 | 5 | 1554.806 CC | | SPH | 800.0000 0.0000 | 555.324 671.757 | | CIR CIR | REFL |
| IMAGE | | INF | | FLT | | 671.757 | | | |

NOTES
Positive radius indicates the center of curvature is to the right
Negative radius indicates the center of curvature is to the left
Dimensions are given in millimeters
Thickness is axial distance to next surface
Image diameter shown above is a paraxial value, it is not a ray traced value aspheric constants $$Z = \frac{(CURV)Y^2}{1 + (1 - (1+K)(CURV)^2 Y^2)^{1/2}} + (A)Y^4 + (B)Y^6 + (C)Y^8 + (D)Y^{10} + (E)Y^{12} + (F)Y^{14} + (G)Y^{16} + (H)Y^{18} + (J)Y^{20}$$

| ASPHERIC | CURV | K E | A F | B G | C H | D J |
|---|---|---|---|---|---|---|
| A-1 | −0.196699E−02 | 0.00000000 5.77273E−33 | 4.71555E−11 4.91517E−38 | 1.80988E−16 0.00000E+00 | 6.26281E−22 0.00000E+00 | 2.51157E−27 0.00000E+00 |
| A-2 | 0.01784111 | 0.00000000 −1.54155E−19 | −7.32381E−08 1.90098E−23 | 1.34142E−11 0.00000E+00 | −2.83704E−14 0.00000E+00 | 1.26372E−16 0.00000E+00 |
| A-3 | 0.02044744 | 0.00000000 1.25363E−16 | 9.96891E−08 6.15908E−24 | −3.66193E−10 0.00000E+00 | 6.82424E−12 0.00000E+00 | −4.72979E−14 0.00000E+00 |

DECENTERING CONSTANTS

| DECENTER | X | Y | Z | ALPHA | BETA | GAMMA | |
|---|---|---|---|---|---|---|---|
| D(1) | 0.0000 | −51.3259 | 0.0000 | 0.0000 | 0.0000 | 0.0000 | (RETU) |

What is claimed is:

1. An apparatus for inspecting a photomask using a light, comprising:
    an illumination source for generating the light which illuminates a target substrate;
    objective optics for receiving and projecting the light which is reflected from the target substrate, the objective optics comprising:
        a first mirror which is arranged to receive and reflect the light which is reflected from the target substrate;
        a second mirror which is arranged to receive and reflect the light which is reflected by the first mirror;
        a third mirror which is arranged to receive and reflect the light which is reflected by the second mirror; and,
        a segmented mirror which is arranged to receive and reflect the light which is reflected by the third mirror, wherein the segmented mirror comprises at least two mirror segments;
    the apparatus further comprising at least one sensor for detecting the light which is projected directly by the 2. The apparatus recited in claim 1, wherein the light comprises extreme ultra-violet (EUV) light.

3. The apparatus recited in claim 1, wherein the second mirror partially obscures the first mirror from the reflected light.

4. The apparatus recited in claim 1, wherein the light reflected by the second mirror passes through an opening in the first mirror.

5. The apparatus recited in claim 1, wherein the first, second, third, and segmented mirrors are, respectively, concave, convex, concave, concave.

6. The apparatus recited in claim 1, wherein the segmented mirror is spherical.

7. The apparatus recited in claim 1, wherein the segmented mirror is aspherical.

8. The apparatus recited in claim 1, wherein the mirror segments comprise a coating.

9. The apparatus recited in claim 1, wherein the mirror segments are fixedly connected.

10. The apparatus recited in claim 1, wherein a numerical aperture of the objective optics is at least 0.2.

11. The apparatus recited in of claim 1, wherein a field of view of the apparatus is at least greater than 120,000 square microns.

12. The apparatus recited in claim 1, wherein a distance between the target substrate and the second mirror is at least 174 millimeters.

13. The apparatus recited in claim 1, wherein a quantity of mirror segments equals a quantity of sensors.

14. Objective optics for inspecting a target substrate using a light, comprising:
   a first mirror which is arranged to receive and reflect the light which is reflected from the target substrate,
   a second mirror which is arranged to receive and reflect the light which is reflected by the first mirror,
   a third mirror which is arranged to receive and reflect the light which is reflected by the second mirror, and
   a segmented mirror which is arranged to receive the light which is reflected by the third mirror and to directly reflect the light to at least one sensor for detecting the light, the segmented mirror comprising at least two mirror segments, wherein a numerical aperture of the objective optics is at least 0.2 and a respective mirror segment in the segmented mirror supports the imaging of a sub-field equal to a size of a single time delay integration sensor.

15. The apparatus recited in claim 14, wherein the light comprises extreme ultra-violet (EUV) light.

16. The objective optics recited in claim 14, wherein the second mirror partially obscures the first mirror from the reflected light.

17. The objective optics recited in claim 14, wherein the light reflected by the second mirror passes through an opening in the first mirror.

18. The objective optics recited in claim 14, wherein the segmented mirror is spherical.

19. The objective optics recited in claim 14, wherein the segmented mirror is aspherical.

20. A method of projecting a light reflected from a target substrate to a sensor, the method comprising:
   receiving and reflecting the light which is reflected from the target substrate using a first mirror;
   receiving and reflecting the light which is reflected from the first mirror using a second mirror;
   receiving and reflecting the light which is reflected from the second mirror using a third mirror;
   receiving and reflecting the light which is reflected from the third mirror using a segmented mirror, wherein the segmented mirror comprises at least two mirror segments and a respective mirror segment in the segmented mirror supports the imaging of a sub-field equal to a size of a single time delay integration sensor; and
   detecting the light which is directly reflected by the segmented mirror to the sensor.

21. The apparatus recited in claim 20, wherein the light comprises extreme ultra-violet (EUV) light.

22. The method recited in claim 20, wherein a numerical aperture of the objective optics is at least 0.2.

23. The method recited in claim 20, wherein the second mirror partially obscures the first mirror from the reflected light.

* * * * *